(12) United States Patent
Schlegel et al.

(10) Patent No.: US 8,012,679 B1
(45) Date of Patent: Sep. 6, 2011

(54) PAPILLOMAVIRUS VACCINES

(75) Inventors: C. Richard Schlegel, Rockville, MD (US); A. Bennett Jenson, Rockville, MD (US)

(73) Assignee: Georgetown University, Washington, DC (US)

( * ) Notice: Subject to any disclaimer, the term of this patent is extended or adjusted under 35 U.S.C. 154(b) by 246 days.

(21) Appl. No.: 08/764,926

(22) Filed: Dec. 16, 1996

Related U.S. Application Data

(60) Division of application No. 08/216,506, filed on Mar. 22, 1994, which is a continuation of application No. 07/903,109, filed on Jun. 25, 1992, now abandoned.

(51) Int. Cl.
*C12Q 1/70* (2006.01)

(52) U.S. Cl. ...... 435/5; 424/204.1; 435/69.3; 435/235.1

(58) Field of Classification Search ............... 530/388.3, 530/389.4; 424/179.1; 435/5, 975
See application file for complete search history.

(56) References Cited

OTHER PUBLICATIONS

Christensen, N.D. et al. Journal of General Virology, vol. 75, p. 2271-2276, 1994.*
Christensen, N.D. et al. Virology, vol. 205, p. 329-335, 1994.*
Christensen, N.D. et al. Journal of Virology, vol. 64, p. 5678-5681, 1990.*
Lin, Y.-L. et al. Virology, vol. 187, p. 612-619, Apr. 1, 1992.*
Kirnbauer, R. et al. Journal of Virology, vol. 67, p. 6929-6936, 1993.*
Bonnez et al (Journal of General Virology 72:1343-1347, 1991).*
"Expression of Vaccinia Recombinant HPV16 L1 and L2 ORF Proteins in Epithelial Cells is Sufficient for Assemble of HPV Virion-like Particles", Zhou et al, Virology 185:251-257, 1991.*
Kirnbauer et al ("Efficient self-assembly of human papillomavirus type 16 L1 and L1-L2 into virus-like particles" Journal of Virology 67:6929, 1993.*
Kirnbauer et al ("A virus-like particle enzyme-linked immunosorbent assay detects serum antibodies in a majority of women infected with human papillomavirus type 16" Journal of the National Cancer Institute 86: 494-499, 1994).*

* cited by examiner

*Primary Examiner* — Mary E Mosher
(74) *Attorney, Agent, or Firm* — Carella, Byrne et al.; Elliot M. Olstein; Raymond J. Lillie

(57) ABSTRACT

Seven polyclonal and monoclonal antibodies were characterized for their ability to react specifically with either conformational or non-conformational epitopes of the HPV-1 virion. Using these antibodies, it was shown that the HPV-1 L1 protein (when expressed by an SV40 vector in cos cells) displayed conformational epitopes characteristic of intact viral particles. In addition, the L1 capsid protein was translocated normally into cell nuclei, was of appropriate size (57kD), and could be isolated in native form by immunoprecipitation techniques. Most importantly, the screening of expressed papillomavirus capsid proteins for reactivity with conformation-dependent antibodies represents a new, general methodology for ensuring that such proteins will be suitable for use in vaccine development or in the serologic detection/typing of human papillomavirus infections.

6 Claims, 4 Drawing Sheets

PAPILLOMAVIRUS VACCINES

This application is a continuation, divisional, of application Ser. No. 08/216,506, filed Mar. 22, 1994, in turn, a continuation of application Ser. No. 07/903,109, filed Jun. 25, 1992 now abandoned.

FIELD OF THE INVENTION

The invention relates to the diagnosis, serotyping, prevention and treatment of viral diseases, particularly papillomavirus infections.

BACKGROUND OF THE INVENTION

Papillomaviruses (PV) are members of the papovavirus family and contain a double stranded circular DNA genome with a typical size of about 7900 base pairs (bp). Human papillomaviruses (HPV) are recognized as a cause of various epithelial lesions such as warts, condylomas and dysplasias. See, Gissman, L. *Cancer Survey* 3:161 (1984); Boshart et al, *ENBO J.* 3:1151 (1984); Romanczuk et al, *J. Virol.* 65:2739-2744 (1991); Jenson et al, In "Papillomaviruses and human cancer" (H. Pfister. Ed.), pp. 11-43, CRC Press (1990); Schlegel, R., "Papillomaviruses and human cancer" In: *Viral pathogenesis* (ed. Fujinami, R.), Seminars in Virology 1:297-306 (1990); and Jenson et al, "Human Papillomaviruses" In Belshe, R. ed. Textbook of human virology, Second Edition: MASS:PSG, 1989:951.

HPVs are grouped into types based on the similarity of their DNA sequence. Two HPVs are taxonomically classified as being of the same type if their DNAs cross-hybridize to greater than 50% as measured by hybridization in solution under moderately stringent hybridization conditions.

A number of distinct papillomaviruses have been shown to infect humans. Papillomaviruses are highly species and tissue-specific, and are characterized by a specific mode of interaction with the squamous epithelia they infect. These small DNA tumor viruses colonize various stratified epithelia like skin and oral and genital mucosa, and induce the formation of self-limiting benign tumors known as papillomas (warts) or condylomas. These tumors are believed to arise from an initial event in the infectious cycle where the virus enhances the division rate of the infected stem cell in the epithelial basal layer, before it is replicated in the differentiating keratinocyte.

The term papillomavirus covers a large number of viruses which are considered responsible for several forms of viral infection ranging from relatively benign warts of the skin or mucous membranes to hyperplasias susceptible to progressing into dysplasias or intra-epithelial neoplasms, and malignant conversion to various forms of cancer, the most significant being that of the female uterine cervix.

A number of HPVs types have been identified. Furthermore, the preferential association of certain HPV types with anatomic location and distinct types of lesions gives support to the hypothesis that different HPV-induced lesions constitute distinct diseases, and that the clinical patterns of lesions express specific biological properties of distinct types of HPVs. Distinctive histological features have been associated with the infection of the skin or mucous membranes by different types of HPVs.

The genomes of different HPV types have been cloned and characterized. In particular, the genomes of two HPV types, HPV 16 and HPV 18, have been found to be associated with about 70% of invasive carcinomas of the uterine cervix.

Human papillomaviruses which infect the genital tract mucosa play a critical role in the development of cervical cancer. See, Lorincz et al, *Obstetrics & Gynecology,* 79:328-337 (1992); Beaudenon et al, *Nature,* 321:246-249 (1986); and Holloway et al, *Gynecol. One.,* 41:123-128 (1991). For example, the majority of humans cervical carcinomas (95%) contain and express HPV DNA and it is the expression of two viral oncoproteins, E6 and E7, which appears to be critical for cellular transformation and maintenance of the transformed state. Despite the detailed knowledge concerning the molecular mechanism of action of these oncoproteins, there is little information available on the biology of papillomavirus infection, including the identity of viral receptors, the control of viral replication and assembly, and the host immune response to virus and virally-transformed cells. An effective vaccine against HPV infection could potentially reduce the incidence of human cervical dysplasia and carcinoma by 90-95%. However, there is no tissue culture system which permits sufficient keratinocyte differentiation to propagate the PV in-vitro. Because of the widespread occurrence of HPV infection, methods for detecting, preventing and treating viral infection is needed.

SUMMARY OF THE INVENTION

A recombinantly produced L1 major capsid protein which mimics conformational neutralizing epitopes on human and animal papilloma virions is provided. The recombinant protein reproduces the antigenicity of the intact, infectious viral particle. The recombinant protein can be utilized to immunoprecipitate antibodies from the serum of patents infected or vaccinated with PV. Neutralizing antibodies to the recombinant protein are also provided. The antibodies are useful for the diagnosis and treatment of papilloma viral infection. The invention additionally provides subviral vaccines for the prevention of human and animal papillomavirus infection.

Purified HPV-1 virions were denatured with SDS and their constituent proteins separated by SDS polyacrylamide gel electrophoresis. The HPV-1 proteins were then transferred electrophoretically to nitrocellulose and reacted with 1:100 dilutions of the rabbit antisera or monoclonal antibodies (ascites fluid). MAB45, which was produced as a hybridoma supernatant, was only diluted 1:10. Primary antibody reactivity was detected using alkaline phosphatase-labelled goat anti-rabbit or anti-mouse IgG (Bio-Rad) at a dilution of 1:1000 in PBSA. Only rabbit antiserum #3 and MAB45, which both recognize denatured HPV-1 virions by ELISA, were found to react significantly with denatured L1 protein (see arrow).

Figure 2:
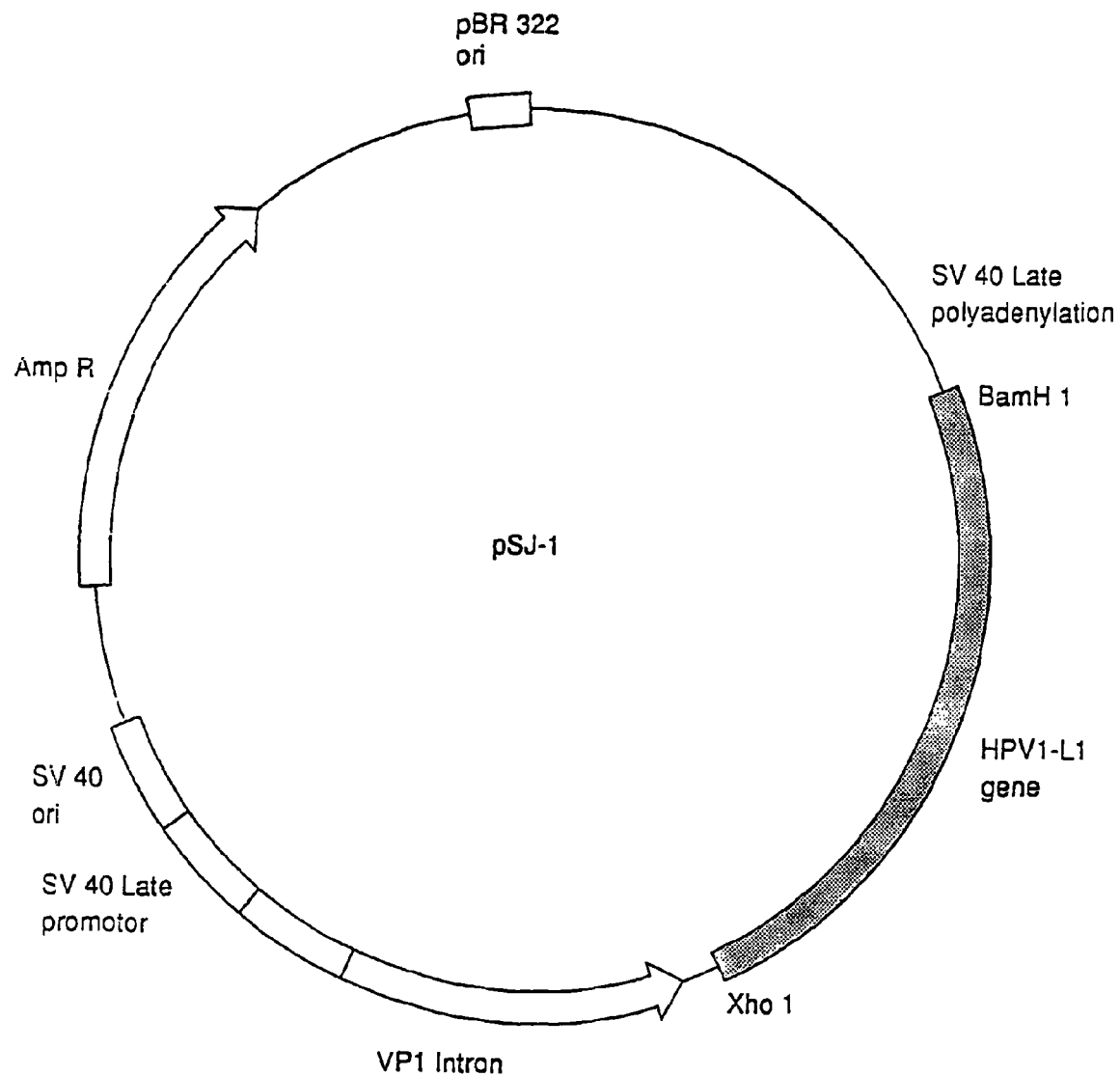

FIG. 2. Construction of SV40 vector, pSJ-1, which expresses the HPV-1 L1 gene.

The L1 gene of HPV-1 was amplified from cloned HPV-1 DNA using 5' and 3' oligonucleotide primers which contained XhoI and BamHI enzyme restriction sites, respectively. The plasmid, designated pSJ-1, contained the HPV-1 L1 gene expressed by the SV40 late promoter. The plasmid also contained the SV40 origin of replication (ori) as well as the SV40 VP1 intron and late polyadenylation signals. The entire pSJ-1 L1 gene was sequenced in its entirety and found to be identical to the genomic HPV-1 L1 sequence.

Figure 3:
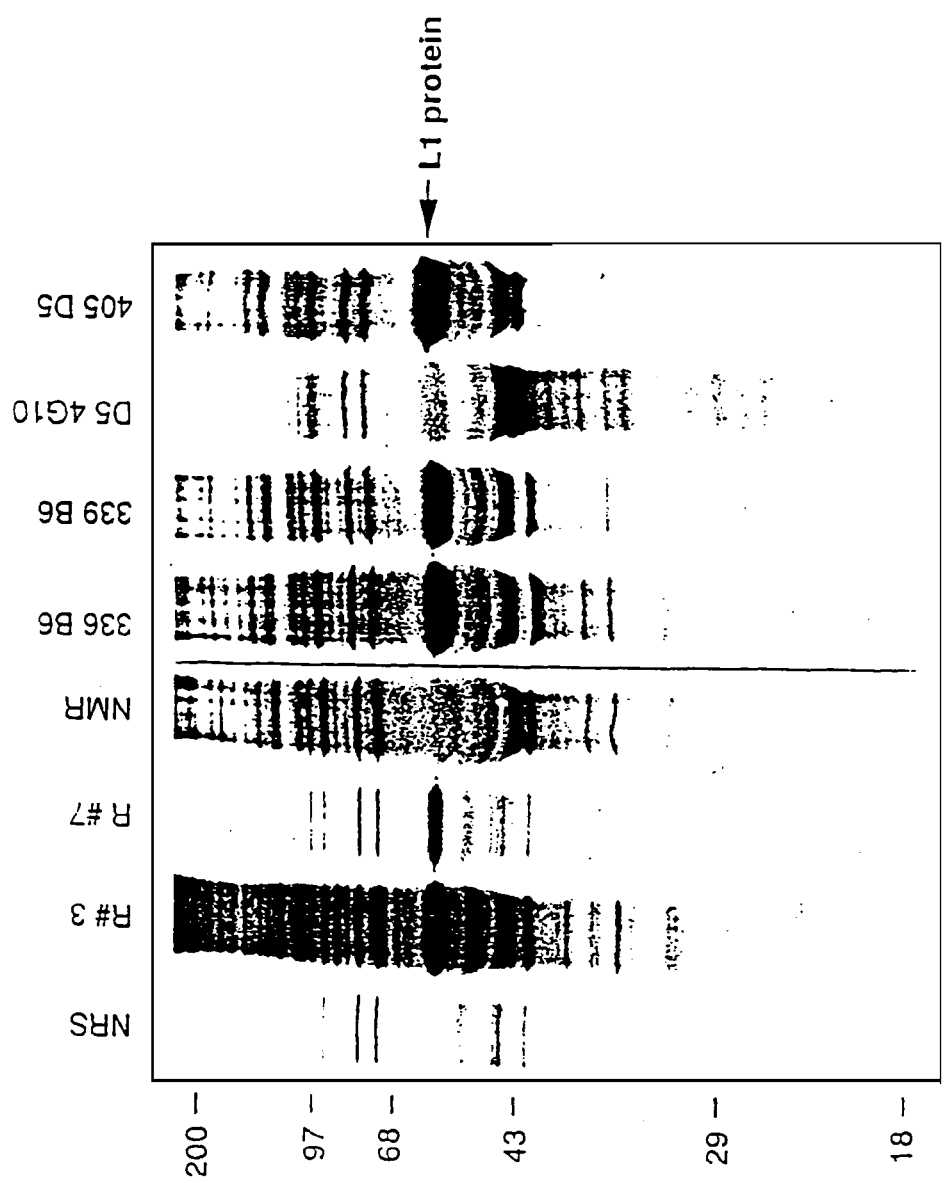

FIG. 3. Immunoprecipitation of HPV-1 L1 protein from cos cells transfected with pSJ-1.

Cos cells, grown in 10 cm diameter plastic plates, were transfected when 80% confluent with 10 μg pSJ-1 plasmid DNA using a calcium phosphate precipitation technique (Graham, F. L., and van der Eb., A. J., Virology 52:456-467 (1973). 48 hr later, the cells were metabolically labelled with 500 μCi/ml$^{35}$ S-methionine for 4 hr in 2.5 ml cysteine and methionine-free medium. The cells were then washed with PBS, extracted with RIPA buffer, and immunoprecipitated with the indicated rabbit antisera or mouse monoclonal antibodies. The immunoprecipitated proteins were then analyzed by SDS-gel electrophoresis and autoradiography. All immune polyclonal antisera and monoclonal antibodies were able to immunoprecipitate L1 protein (see arrow). Lanes 1 and 4 show the absence of L1 protein when extracts were precipitated with either non-immune rabbit serum (lane 1) or with non-immune murine serum (lane 4).

Figure 4:
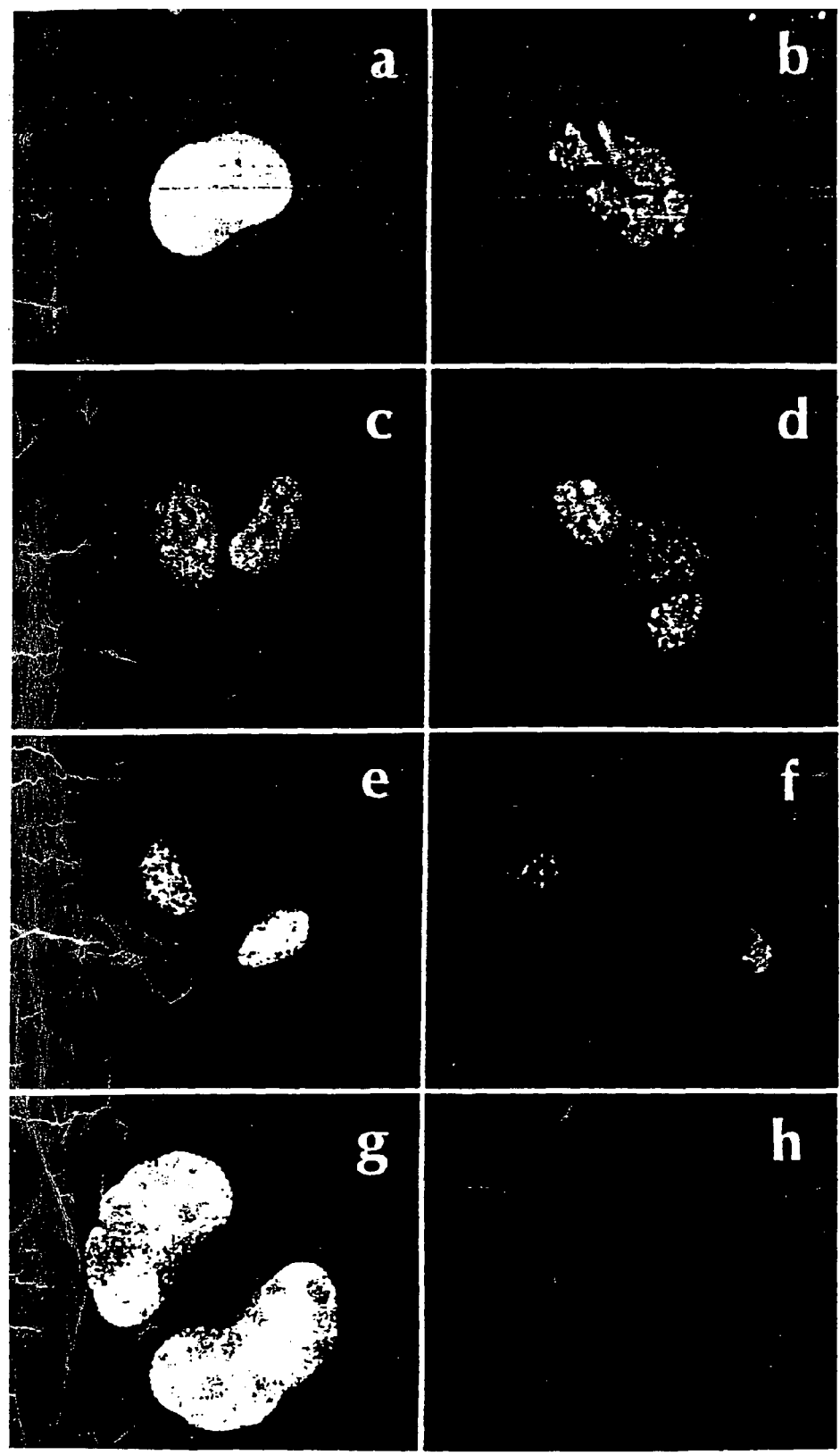

FIG. 4. Immunofluorescent staining of cos cells transfected with pSJ-1.

Cos cells grown on glass coverslips were transfected with 10 μg pSJ-1 as described in FIG. 3. After 48 hr, the coverslips were washed with PBS, fixed in cold acetone, and reacted with 1:250 dilutions of rabbit antisera or mouse monoclonal antibodies. The reacted primary antibodies were stained with FITC-labeled goat anti-IgG at the dilution of 1:10 in PBS (Cappel). Nuclei of approximately 5-10% of transfected cos cells were positive by immunofluorescence. The evaluated antibodies were R#3 (panel a), R#7 (panel b), MAB45 (panel c), 334B6 (panel d), 339B6 (panel e), D54G10 (panel f), and 405D5 (panel g). All antisera were non-reactive with cos cells transfected with the parent pSVL vector lacking the HPV-1 L1 gene, including R#3 (panel h).

DESCRIPTION OF THE PREFERRED EMBODIMENTS

Methods and compositions are provided for the prevention, detection and treatment of papillomavirus (PV) infection. The methods are based upon the production of a recombinant L1 major capsid protein which is capable of reproducing the conformational neutralizing epitopes on human and animal papillomavirus virions. The invention is further drawn to antigenic fragments of such recombinant L1 proteins.

Although papillomaviruses infect a wide variety of vertebrate species, they exhibit a remarkable conservation of genomic organization and capsid protein composition. Papillomaviruses consist of small (about 55 nm), non-enveloped virions which surround a genome of double-stranded, circular DNA. The genome is approximately 8,000 bp in length and can be divided into equal-length "early" and "late" regions. The "early" region encodes 7-8 genes involved in such processes as viral DNA replication (the E1 and E2 genes), RNA transcription (the E2 gene), and cell transformation (the E5, E6 and E7 genes). The "late" region encodes two structural proteins, L1 and L2, which represent the major and minor capsid proteins, respectively. All of the "early" and "late" genes are transcribed from the same strand of viral DNA.

There are a variety of PV types known in the art. Further, particular types of PVs are associated with particular infections such as flat warts, cutaneous warts, epidermodysplasia verruciformis, lesions and cervical cancer. Over 50 different HPV types have been identified in clinical lesions by viral nucleotide sequence homology studies. See, for example, Jenson et al, "Human papillomaviruses" In: Belshe, R. ed., Textbook of human virology, Second Edition, MASS: PSG, 1989:951 and Kremsdorf et al, *J. Virol.*, 52:1013-1018 (1984). The HPV type determines, in part, the site of infection, the pathological features and clinical appearance as well as the clinical course of the respective lesion.

The L1 protein represents the most highly conserved protein of all the papillomavirus proteins. The nucleotide sequence of the L1 open reading frames of BPV-1, HPV-1A, and HPV-6B are given in U.S. Pat. No. 5,057,411, which disclosure is incorporated herein by reference. Furthermore, it is noted that L1 proteins and fusion proteins have been produced recombinantly. However, prior to the present invention, it was not known that L1 proteins with sufficient fidelity to maintain a conformation equivalent to that found in intact papillomavirus virions could be produced. Previously, recombinant L1 protein was produced as linear molecules which were incapable of protecting against papillomavirus infection. The present invention, in contrast, provides conformationally correct protein which is capable of inducing neutralizing antibodies which protect against animal and human papillomaviruses.

Because it is believed that there is little or no cross-immunity for PV types and immunity to infection is PV type-specific, it will be necessary to produce recombinant L1 protein for each specific PV type upon which protection or treatment is needed. However, due to the homology between the L1 proteins and genes, hybridization techniques can be utilized to isolate the particular L1 gene of interest. Nucleotide probes selected from regions of the L1 protein which have been demonstrated to show sequence homology, can be utilized to isolate other L1 genes. Methods for hybridization are known in the art. See, for example, *Nucleic Acid Hybridization, A Practical Approach*, IRL Press, Washington, D.C. (1985); *Molecular Cloning, A Laboratory Manual*, Maniatis et al, eds., Cold Spring Harbor Laboratory, Cold Spring Harbor, N.Y. (1982); and *Molecular Cloning, A Laboratory Manual*, Sambrook et al, eds., Cold Spring Harbor Laboratory, Second Edition, Cold Spring Harbor, N.Y. (1989). Alternatively, PCR methods can be utilized to amplify L1 genes or gene fragments. See, for example, U.S. Pat. Nos. 4,683,195; 4,683,202; and 4,800,159.

Virus particles can also be isolated for a particular papillomavirus type, the DNA cloned, and the nucleic acid sequences encoding L1 proteins isolated. Methods for isolation of viral particles and cloning of virus DNAs have been reported. See, for example, Heilman et al (1980) *J. Virology* 36:395-407; Beaudenon et al (1986) *Nature* 321:246-249; Georges et al (1984) *J. Virology* 51:530-538; Kremsdorf et al (1984) *J. Virology* 52:1013-1018; Clad et al (1982) *Virology* 118:254-259; DeVilliers et al (1981) *J. Virology* 40:932-935; and European Patent Application 0133123.

Alternatively, the L1 protein for a particular papillomavirus can be isolated, the amino acid sequence determined and nucleic acid probes constructed based on the predicted DNA sequence. Such probes can be utilized in isolating the L1 gene from a library of the papillomavirus DNA. See, for example, Suggs et al (1981) PNAS 78(11):6613-6617. See also, Young and Davis (1983) PNAS 80:1194.

Since the recombinant L1 protein must be of suitable conformation to mimic that of the intact virus particle, the expression system is crucial to the invention. An expression system must be utilized which produces L1 protein in the correct conformation. That is, the recombinant L1 protein reproduces the antigenicity of intact infectious virus particles. Such expression systems should also produce high levels of capsid protein. Generally, the expression system will comprise a vector having the L1 protein of interest and the appropriate regulatory regions as well as a suitable host cell. Typically a suitable host will be one which provides eucaryotic mechanisms for processing of the proteins.

Ideally, a strong promoter is utilized for high expression of the recombinant protein. Of particular interest is the pSVL vector. The pSVL vector contains an SV40 origin of replication and when transfected in COS cells, which express Large T antigen, replicates to a high copy number.

Alternatively, baculovirus vectors can be utilized. A baculovirus system offers the advantage that a large percentage of cells can be induced to express protein due to the use of infection rather than transfection techniques. While baculovirus is an insect virus and grows in insect cells (SF9), these cells retain many of the eucaryotic mechanisms for processing of proteins including glycosylation and phosphorylation which may be important for generating proteins of appropriate conformation. Baculovirus vector systems are known in the art. See, for example, Summers and Smith, Texas Agricultural Experimental Bulletin No. 1555 (1987); Smith et al, *Mol. Cell. Biol.* 3:2156-2165 (1985); Posse, *Virus Research* 5:4359 (1986); and Matsuura, *J. Gen. Virol.* 68:1233-1250 (1987).

For expression in an appropriate expression system, the L1 gene is operably linked into an expression vector and introduced into a host cell to enable the expression of the L1 protein by that cell. The gene with the appropriate regulatory regions will be provided in proper orientation and reading frame to allow for expression. Methods for gene construction are known in the art. See, in particular, *Molecular Cloning, A Laboratory Manual*, Sambrook et al, eds., Cold Spring Harbor Laboratory, Second Edition, Cold Spring Harbor, N.Y. (1989) and the references cited therein.

A wide variety of transcriptional and translational regulatory sequences may be employed. The signals may be derived from viral sources, where the regulatory signals are associated with a particular gene which has a high level of expression. That is, strong promoters, for example, of viral or mammalian sources, will be utilized. In this manner, the optimum conditions for carrying out the invention include the cloning of the L1 gene into an expression vector that will overexpress conformationally-dependent epitopes of the L1 protein in transfected or infected target cells.

The recombinant L1 protein is confirmed by reaction with antibodies or monoclonal antibodies which react or recognize conformational epitopes present on the intact virion. In this manner, the L1 protein can be verified as having the suitable conformation. Thus, other expression vectors and expression systems can be tested for use in the invention.

Once the L1 protein of suitable conformation has been expressed, antibodies can be raised against the recombinant protein or antigenic fragments thereof. The antibodies of the present invention may be prepared using known techniques. Monoclonal antibodies are prepared using hydridoma technology as described by Kohler et al, *Nature* 256:495 (1975); Kohler et al, *Eur. J. Immunol.* 6:511 (1976); Kohler et al, *Eur. J. Immunol.* 6:292 (1976); Hammerling et al, in: *Monoclonal Antibodies and T-Cell Hybridomas*, Elsavier, N.Y., pages 563-681 (1981). Such antibodies produced by the methods of the invention are capable of protecting against PV infection.

The term "antibody" includes both polyclonal and monoclonal antibodies, as well as fragments thereof, such as, for example, Fv, Fab and F(ab)$_2$ fragments which are capable of binding antigen or hapten. Such fragments are typically produced by proteolytic cleavage, such as papain, to produce Fab fragments or pepsin to produce F(ab)$_2$ fragments. Alternatively, hapten-binding fragments can be produced through the application of recombinant DNA technology or through synthetic chemistry.

As indicated, both polyclonal and monoclonal antibodies may be employed in accordance with the present invention. Of special interest to the present invention are antibodies which are produced in humans or are "humanized" (i.e., non-immunogenic in a human) by recombinant or other technology. Humanized antibodies may be produced, for example, by placing an immunogenic portion of an antibody with a corresponding, but non-immunogenic portion, chimeric antibodies. See, for example, Robinson et al, International Patent Publication PCT/US86/02269; Akira et al, European Patent Application 184,187; Taniguchi, M. European Patent Application 171,496; Morrison et al, European Patent Application 173,494; Neuberger et al, PCT Application WO86/01533; Cabilly et al, European Patent Application 125,023; Better et al, *Science* 240:1041-1043 (1988); Liu et al, *PNAS* 84:3439-3443 (1987); Liu et al, *J. Immunol.* 139: 3521-3526 (1987); Sun et al, *PNAS* 84:214-218 (1987); Nishimura et al, *Cancer Research* 47:999-1005 (1987); Wood et al, *Nature* 314:446-449 (1985); and Shaw et al, *J. National Cancer Inst.* 80:1553-1559 (1988). General reviews of "humanized" chimeric antibodies are provided by Morrison, S. L. *Science* 229:1202-1207 (1985) and by Oi et al, *BioTechniques* 4:214 (1986).

The antibodies, or antibody fragments, of the present invention can be utilized to detect, diagnose, serotype, and treat papillomavirus infection. In this manner, the antibodies or antibody fragments are particularly suited for use in immunoassays.

Antibodies, or fragments thereof, may be labeled using any of a variety of labels and methods of labeling. Examples of types of labels which can be used in the present invention include, but are not limited to, enzyme labels, radioisotopic labels, non-radioactive isotopic labels, fluorescent labels, toxin labels, and chemiluminescent labels.

Examples of suitable enzyme labels include malate hydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, glucoamylase, acetylcholine esterase, etc.

Examples of suitable radioisotopic labels include $^3$H, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$P, $^{47}$Sc, and $^{109}$Pd.

Examples of suitable fluorescent labels include a $^{152}$Eu label, a fluorescein label, an isothiocyanate label, a rhodamine label, a phycoerythrin label, a phycocyanin label, and allophycocyanin label, an o-phthaldehyde label, an fluorescamine label, etc.

Examples of suitable toxin labels include diphtheria toxin, ricin, and cholera toxin. Examples of chemiluminescent labels include a luminal label, an isoluminal label, an aromatic acridinium ester label, and imidazole label, and acridinium salt label, an oxalate ester label, a luciferin label, a luciferase label, an aequorin label, etc.

Those of ordinary skill in the art will know of other suitable labels which may be employed in accordance with the present invention. The binding of these labels to antibodies or fragments thereof can be accomplished using standard techniques commonly known to those of ordinary skill in the art. Typical techniques are described by Kennedy, J. H., et al *Clin. Chim. Acta* 70:1-31 (1976), and Schurs, A. H. W. M., et al, *Clin. Chim. Acta* 81:1-40 (1977). Coupling techniques mentioned in the latter are the glutaraldehyde method, the periodate method, the dimaleimide method, the m-maleimidobenzyl- N-hydroxy-succinimide ester method, all these methods incorporated by reference herein.

The detection of the antibodies (or fragments of antibodies) of the present invention may be improved through the use of carriers. Well-known carriers include glass, polystyrene, polypropylene, polyethylene, dextran, nylon, amylases, natural and modified celluloses, polyacrylamides, agaroses and magnetite. The nature of the carrier can be either soluble to some extent or insoluble for the purposes of the present invention. Those skilled in the art will note many other suitable carriers for binding monoclonal antibody, or will be able to ascertain the same by use of routine experimentation.

By raising antibodies against L1 proteins which mimic the antigenicity of papillomavirus virions, the antibodies raised against such recombinant proteins are neutralizing and protective antibodies. The antibodies are able to prevent subsequent infection of the same type of papillomaviruses from which the L1 protein was derived. That is, if a recombinant L1 protein from papillomavirus type 16 is utilized to raise antibodies, these antibodies will protect against subsequent infection of papillomavirus type 16. Thus, the method of the present invention provides for the prevention, treatment or detection of any HPV type.

The antibodies of the invention can be utilized to determine HPV types by serotyping as set forth in Jenson et al, *J. Cutan. Pathol.* 16:54-59 (1989). Determining the HPV type may be clinically important for determining the putative biological potential of some productively infected HPV-associated lesions, particularly benign and low-grade premalignant anogenital tract lesions. Thus, the present invention makes it possible to treat and prevent infection of any type of PV from which the L1 gene can be obtained and neutralizing antibodies obtained.

The invention also provides for pharmaceutical compositions as the antibodies can also be utilized to treat papillomavirus infections in mammals. The antibodies or monoclonal antibodies can be used in pharmaceutical compositions to target drug therapies to sites of PV infection. In this manner, the drugs or compounds of interest are linked to the antibody to allow for targeting of the drugs or compounds. Methods are available for linking antibodies to drugs or compounds. See, for example, EP 0,146,050; EP 0,187,658; and U.S. Pat. Nos. 4,673,573; 4,368,149; 4,671,958 and 4,545,988.

Such drug therapies include antiviral agents, toxic agents and photoactivatable compounds, such as coumarin, psoralen, phthalocyanimes, methylene blue, eosin, tetracycline, chlorophylls, porphyrins and the like. Such groups can be attached to the antibodies by appropriate linking groups. Antibody conjugates containing a photoactivatable compound are administered followed by irradiation of the target cells.

The antibody or antibody conjugates of the present invention can be formulated according to known methods to prepare pharmaceutically useful compositions such as by admixture with a pharmaceutically acceptable carrier vehicle. Suitable vehicles and their formulation are described, for example, in Remington's Pharmaceutical Sciences (16th Ed., Osol, A. Ed., Mack Easton Pa. (1980)). To form a pharmaceutically acceptable composition suitable for effective administration, such compositions will contain an effective amount of antibody, either alone, or with a suitable amount of carrier vehicle.

The therapeutic or diagnostic compositions of the invention will be administered to an individual in therapeutically effective amounts. That is, in an amount sufficient to diagnose or treat PV infection. The effective amount will vary according to the weight, sex, age and medical history of the individual. Other factors include, the severity of the patient's condition, the type of PV, mode of administration, and the like. Generally, the compositions will be administered in dosages ranging from about 0.01 to about 2 picomoles/ml, more generally about 0.001 to about 20 picomoles/ml.

The pharmaceutically prepared compositions may be provided to a patient by any means known in the art including oral, intranasal, subcutaneous, intramuscular, intravenous, intraarterial, parenteral, etc.

Another aspect of the present invention involves the development of PV type-specific vaccines. The vaccines of the invention are those that contain the necessary antigenic determinants to induce formation of neutralizing antibodies in the host; possess high immunogenic potential; are safe enough to be administered without danger of clinical infection; devoid of toxic side-effects; suitable for administration by an effective route, for example, oral, intranasal, topical or parenteral; mimics the circumstances of natural infection; stable under conditions of long-term storage; and, compatible with the usual inert vaccine carriers.

The vaccines of the present invention include the conformationally correct recombinant L1 proteins or fragments thereof which provide the conformational epitopes present on the intact virions. Such amino acid sequences of the L1 protein comprise the antigenic component of the vaccine. It may be necessary or preferable to covalently link the antigen to an immunogenic carrier, i.e., bovine serum albumin or keyhole limpet hemocyanin. The vaccines of the invention may be administered to any mammal susceptible to infection with the papillomavirus. Human and non-animal mammals may benefit as hosts.

Administration of the vaccines may be parenteral, but preferably oral or intranasal, depending upon the natural route of infection. The dosage administered may be dependent upon the age, health, weight, kind of concurrent treatment, if any, and nature and type of the papillomavirus. The vaccine may be employed in dosage form such as capsules, liquid solutions, suspensions, or elixirs, for oral administration, or sterile liquid formulations such as solutions or suspensions for parenteral or intranasal use. An inert, immunologically acceptable carrier is preferably used, such as saline or phosphate-buffered saline.

The vaccines will be administered in therapeutically effective amounts. That is, in amounts sufficient to produce a protective immunological response. Generally, the vaccines will be administered in dosages ranging from about 0.1 mg protein to about 20 mg protein, more generally about 0.01 mg to about 100 mg protein. A single or multiple dosages can be administered.

The method of the present invention makes possible the preparation of subviral vaccines for preventing papillomavirus infection. Further, by following the methods of the invention, vaccines for any immunogenic type of specific papillomavirus can be made.

As more than one PV type may be associated with PV infections, the vaccines may comprise L1 antigenic amino acids from more than one type of PV. For example, as HPV 16 and 18 are associated with cervical carcinomas, a vaccine for cervical neoplasias may comprise L1 protein of HPV 16; of HPV 18; or both HPV 16 and 18.

In fact, a variety of neoplasias are known to be associated with PV infections. For example, HPVs 3a and 10 have been associated with flat warts. A number of HPV types have been reported to be associated with epidermodysplasia verruciformis (EV) including. HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes. See, for example, Kremsdorf et al, *J. Virol.* 52: 1013-1018 (1984); Beaudenon et al, *Nature* 321:246-249 (1986); Heilman et al, *J. Virol.* 36:395-407 (1980); and DeVilliers et al, *J. Virol.* 40:932-935 (1981). Thus, vaccine formulations may comprise a mixture of L1 proteins from different PV types depending upon the desired protection.

In the same manner, the pharmaceutical compositions may contain a mixture of antibodies to different PV types.

As indicated, the L1 protein of the invention can be utilized for serotyping.

That is, monoclonal antibodies capable of reacting with conformationally correct L1 protein can be produced which can be used to serotype PV. In this manner, tissue or serum can be obtained from a patient and analyzed for the ability to immunoprecipitate such antibodies In a broader sense, the antibodies can be used for serological screening. In this manner, populations of individuals can be tested for the ability to immunoprecipitate conformationally correct antibodies. Specific HPV type antibody responses can be determined.

The invention lends itself to the formulation of kits, particularly for the detection and serotyping of HPV. Such a kit would comprise a carrier being compartmentalized to receive in close confinement one or more containers, each container having antibodies for a particular HPV type or a mixture of antibodies for a variety of known HPV types. Other containers may contain means for detection such as enzyme substrates, labelled antigen/anti-antibody and the like.

For serological testing, the kits will comprise the conformationally correct recombinant L1 protein. Such a kit could also be utilized for vaccines.

Having now generally described the invention, the following examples are offered by way of illustration and not intended to be limiting unless otherwise specified.

EXPERIMENTAL

Example 1

Materials and Methods

Animals

Female, athymic (nu/nu) mice were purchased from Harlan Sprague Dawley, Madison Wis., and used for xenograft transplants when 6 to 8 weeks old.

Virus

BPV-1 was purified from experimentally-induced bovine cutaneous fibropapillomas as described by Lancaster, W. D. and Olson, D., *Demonstration of two distinct classes of bovine papillomavirus.* Virology, 89, 372-279 (1978) (1978). The virus was stored at −80° C. until used.

Antibodies

All serum samples were heat-inactivated at 56° C. for 30 min. Each antibody preparation was evaluated for reactivity with intact and disrupted BPV-1 particles (Table I) before testing for neutralization of BPV-1 induced transformation of C127 cells and xenografts.

Bovine polyclonal antibodies. Bovine sera were obtained from calves either vaccinated with BPV-1 L1 fusion proteins or experimentally-infected with BPV-1.

Holstein X Angus calves were immunized with different formulations of a recombinant BPV-1 L1::B-galactosidase vaccine (Jin, X. W., Cowsert, L., Marshall D., Reed, D., Pilacinski, W., Lim, L. and Jenson, A. B., *Bovine serological response to a recombinant BPV-1 major capsid protein vaccine. Intervirology,* 31, 345-354 (1990)). The cloned L1 gene begins 76 bp down stream from the start codon of the L1 open reading frame at nucleotide 5686 and is terminally fused to the *E. coli* B-galactosidase gene (Pilacinski, W. P., Glassman, D. L., Richard, A. K. Sadowski, P. L. and Alan, K. R., *Cloning and expression in Escherichia coli of the bovine papillomavirus L1 and L2 open reading frames. Bio/Technol.,* 2, 356-360 (1984)). Calves were vaccinated on days 0 to 21, and challenged by intradermal inoculation of 2 sites with $10^{10}$ BPV-1 particles on day 56 (Jin, X. W., Cowsert, L., Marshall D., Reed, D., Pilacinski, W., Lim, L. and Jenson, A. B., *Bovine serological response to a recombinant BPV-1 major capsid protein vaccine. Intervirology,* 31, 345-354 (1990)). The calves were bled on days 3 (designated as pre-bleed), 55 (bleed 1) and 104 (bleed 2) days of the trial and the sera tested for reactivity with intact and disrupted BPV-1 particles by ELISA. Although 90% and 58% of calves developed antibody responses to internal and external BPV-1 capsid epitopes respectively, all calves developed fibromas.

Two steer (926 and 921), acquired as calves from a sequestered herd of cattle without prior exposure to BPV-1 or BPV-2, were inoculated at multiple sites with finely ground homogenates of BPV-1 induced fibropapillomas. Fibropapillomas developed in the scarified sites and persisted for varying lengths of time before undergoing spontaneous regression. The sera used in this experiment were collected during the earliest signs of fibropapilloma regression in both animals.

Rabbit polyclonal antibodies. Rabbit anti-sera were prepared by inoculation with either intact BPV-1 or BPV-2 virions, or denatured BPV-1 particles and then bled 2 weeks after the final immunization (Jenson, A. B. Rosenthal, J. D., Olson, C., Pass, F. W., Lancaster W. D. and Shah, K., *Immunologic relatedness of papillomaviruses from different species. J. Nat. Cancer Inst.,* 64, 495-500 (1980), Jenson, A. B., Kurman, R. J. and Lancaster, W. D., *Detection of papillomavirus common antigens in lesions of the skin and mucosa. Clinics In Dermatol.,* 3, 56-63 (1985); Cowsert, L. M., Lake, P. and Jenson, A. B., *Topographical and conformational epitopes of bovine papillomavirus type 1 defined by monoclonal antibodies. J. Nat. Cancer Inst.,* 79 1053-1057 (1987)).

Murine monoclonal antibodies. Two murine MAbs, 13D6 and JG, were also used to test for neutralization. 13D6 recognizes conformational epitopes on BPV-1, BPV-2 and deer papillomavirus (DPV) intact particles (Cowsert, L. M., Lake, P. and Jenson, A. B., *Topographical and conformational epitopes of bovine papillomavirus type 1 defined by monoclonal antibodies. J. Nat. Cancer Inst.,* 79 1053-1057 (1987)), whereas JG recognizes a BPV-1 type-specific linear epitope internal to the capsid (data not shown).

TABLE I

ELISA REACTIVITY OF BOVINE, RABBIT AND HUMAN SERA AND MURINE MAbs WITH INTACT AND DISRUPTED BPV-1 PARTICLES

| Serum[1] or | BPV-1 particles | |
|---|---|---|
| MAb samples | Intact | Disrupted |
| Vaccinated calves[2] | | |
| 163 | | |
| Pre-bleed | 0.002 | 0.016 |
| 1 | 0.041 | 0.925 |
| 2 | 0.312 | 1.472 |
| 173 | | |
| Pre-bleed | 0.036 | 0.066 |
| 1 | 0.101 | 1.222 |
| 2 | 0.182 | 1.249 |

TABLE I-continued

ELISA REACTIVITY OF BOVINE, RABBIT AND
HUMAN SERA AND MURINE MAbs WITH INTACT
AND DISRUPTED BPV-1 PARTICLES

| Serum[1] or | BPV-1 particles | |
|---|---|---|
| MAb samples | Intact | Disrupted |
| Rabbit[3] | | |
| NRS | 0.065 | 0.073 |
| BPV-1 | 1.454 | 0.095 |
| BPV-2 | 1.621 | 0.085 |
| BPV-1 (SDS) | 0.319 | 1.358 |
| MAbs | | |
| 13D6 | 0.629 | 0.004 |
| JG | 0.004 | 0.423 |
| Hyperimmune steers[4] | | |
| 926 | 0.296 | 0.033 |
| 921 | 0.397 | 0.202 |
| Human | | |
| 1 | 0.964 | 0.036 |
| 2 | 0.554 | 0.247 |

[1]RBPV-1 and RBPV-2 were diluted 1/2000; all other samples were diluted 1/50.
[2]Pre, pre-bleed sera from calves 163 and 173; 1, sera of calves 163 and 173 at the time of challenge with BPV-1 virions; 2, sera of calves 163 and 173 at end of the vaccine trial.
[3]NRS, normal rabbit serum; BPV-1 (SDS) rabbit serum prepared against SDS-disrupted BPV-1.
[4]Steers (926 and 921), serum of steer inoculated at 24 different cutaneous sites with BPV-1 homogenates.

Neutralization Assays

Two assays (xenografts in athymic mice and murine C127 cells cultures) for detecting antibody-mediated neutralization of infectious PV virions were compared for specificity.

Xenograft assay. To assay for neutralization of BPV-1 infectivity, a 1:10 dilution of polyclonal anti-sera in PBS was added to aliquots of infectious BPV-1 in PBS and incubated for 1 hr at 37° C. BPV-1 in PBS alone was included as a positive control for infectivity. Bovine fetal skin chips (5 to 10×2-x 2-mm pieces) were added to each dilution and incubated for 1 hr at 37° C.

The chips were transplanted under the renal capsule of athymic mice and cyst size (in mm) and morphology of its lining epithelium was determined after 60 days. Cyst sizes were calculated as geometric mean diameters (BMDs) by calculating the cubic root of the length×width×height of cysts in mm.

Statistical analysis was accomplished by determining the means of the GMDs of cysts and fibropapillomas for each anti-serum and was compared with those for untreated controls by using the Student's t-test.

C127 cells assay. Murine C127 cells were obtained from ATCC, Rockville, Md., and grown as described by (Dvoretzky, I., Shober, R., Chattopadhy, S. K. and Lowy, D. R., *A quantitative in vitro focus-forming assay for bovine papillomavirus*. Virology, 103, 369-375 (1980)). The neutralization assays were carried out in Petri dishes (100 mm). C127 cells were seeded at approximately $10^5$ to $5 \times 10^5$ cells, which were allowed to become 75 to 80% confluent, BPV-1 virions ($10^3$ focus-forming units [FFU]) were then incubated with either 0.5 ml DMEM as a positive control for infectivity or an equal volume of the MAb or polyclonal anti-serum (diluted 1:5) at 37° C. for 1 hr prior to inoculation of C127 cells. After 1½ hrs adsorption. 10% FBS supplemented MEM was added to each dish. The medium was replenished the next day and then 3 times each week for 17 to 19 days, at which time the dishes were fixed and stained 0.1% methylene blue in methanol to count the number of FF per dish. Controls included fetal calf sera and serum from a steer that had no history of fibropapillomas.

Results

The specificity of 2 different assay systems, xenografts and C127 cells, for measuring the neutralization of BPV-1 infection were compared using selected animal sera and murine MAbs. The sera and MAbs tested were: (1) sera from rabbits and cattle immunized and/or infected with intact BPV-1 and BPV-2 virions (the immune systems were exposed to both conformational and linear BP-1 capsid surface epitopes); (2) sera from rabbits and cattle immunized with denatured BPV-1 virions and L1 fusion proteins respectively (the immune systems were exposed to denatured/linear BPV-1 capsid epitopes); (3) selected sera from humans that reacted with intact BPV-1; and (4) MAbs that define BPV-1 conformational surface epitopes and epitopes that are internal to the BPV-1 capsid.

Epitope Topography

The sera evaluated in our study were tested initially for reactivity with both intact and disrupted BPV-1 capsids, thus defining the topographical location of the corresponding epitopes as either external or internal to the BPV-1 capsid as previously described (Cowsert, L. M., Lake, P. and Jenson, A. B., *Topographical and conformational epitopes of bovine papillomavirus type 1 defined by monoclonal antibodies*. J. Nat. Cancer Inst., 79 1053-1057 (1987)). (Table I).

Rabbit sera produced against intact BPV-1 or BPV-2 virions and sera from steers inoculated at multiple sites with infectious homogenates of BPV-1 induced fibropapillomas as well as MAb 13D6 reacted primarily with intact virions. The two human sera selected for this study reacted primarily with intact BPV-1 particles.

Rabbit serum prepared against SDS-disrupted BPV-1 viral particles, and sera (bleed 2) from calves 163 and 173 at the end of the vaccine trial, 48 days after challenge with BPV-1 virions, reacted with both intact and disrupted viral particles. Calf 163 serum (bleed 1), immediately prior to challenge with infectious BPV-1 virions, reacted only with disrupted BPV-1 particles. MAb JG reacted only with disrupted BPV-1 virions.

Pre-bleed/normal rabbit and bovine sera (calves 163 and 173 did not react either with intact or with disrupted BPV-1 virions by ELISA.

Neutralization Assays

Two different assays were compared for neutralization of BPV-1 infectivity by the hyperimmune sera and MAbs: (i) xenografts in athymic mice, and (ii) C127 cell cultures.

Xenograft neutralization assay. Polyclonal antisera (non-absorbed) as well as negative control sera were tested for the neutralization of BPV-1 infectivity of bovine fetal skin transplanted beneath the renal capsule of athymic mice. Effective neutralization was determined by comparing cyst size and microscopic morphology (Table II).

Bovine fetal skin chips were incubated with BPV-1 which had been preincubated for 1 hr with dilutions of the various polyclonal antisera. The chips were grafted sub-renally in athymic mice, and average geometric mean diameters of cyst sizes were determined 60 days later (Table II). A large and significant reduction in cyst size was obtained for the sera from 2 rabbits inoculated with intact BPV-1 or BPV-2 and both steer polyclonal anti-sera collected from animals with regressing BPV-1-induced fibropapillomas. Neither polyclonal anti-serum from the rabbit inoculated with denatured BPV-1 particles nor pre-bleed, challenge or post-challenge bovine sera from the recombinant vaccination study in calves and a significant effect on cyst size at the dilution tested. Human sera and MAbs reactive with intact BPV-1 particles or linear epitopes of BPV-1 did not result in cyst-size reduction.

C127 cell neutralization assay. Pre-bleed rabbit and calf 163 and 173 sera, hyperimmune rabbit serum prepared against SDS-disrupted BPV-1 virions, both human sera, and calf sera (163 and 173) following vaccination but immediately prior to challenge with BPV-1, did not neutralize FF of C127 cells by BPV-1 virions (Table III). However, rabbit sera produced by immunization with intact BPV-1 and BPV-2 had neutralizing titers of $10^6$ and $10^4$ respectively, and the hyperimmune steer sera had a neutralizing titer of $10^6$ (926) to $10^3$ (921). Calves 163 and 173 sera at the end of the vaccination trial had a neutralizing titer of less than $10^1$, probably because of exposure to infectious challenge virus, rather than a maturing immune response against the vaccine.

Neither fetal calf sera nor selected adult steer serum from non-immune animals inhibited FF in C127 cells.

TABLE II

CYST SIZE AND MORPHOLOGY OF BPV-1 INDUCED XENOGRAFTS DEVELOPING AFTER VARIOUS SERUM PRETREATMENTS OF INFECTIOUS BPV-1

| Serum or MAb samples[1] | Cyst size[2] (mean and SEM in mm) | Morphology[3] |
|---|---|---|
| Vaccinated calves | | |
| 163 | | |
| Pre-bleed | 5.8 (0.9)[4] | 5/6/6 |
| 1 | 4.0 (0.4) | 4/4/4 |
| 2 | 4.6 (0.5)[4] | 5/6/6 |
| 173 | | |
| Pre-bleed | 6.7 (0.8)[4] | 6/6/6 |
| 1 | 5.2 (0.7)[4] | 6/6/6 |
| 2 | 5.3 (0.6)[4] | 6/6/6 |
| Rabbit | | |
| NRS | 5.8 (0.6)[4] | 8/8/8 |
| BPV-1 | 3.5 (0.2)[5,6] | 0/10/10 |
| BPV-2 | 3.3 (0.5)[5,6] | 1/6/6 |
| BPV-1 (SDS) | 8.3 (0.5)[4,5] | 4/4/4 |
| MAbs | | |
| 13D6 | 4.4 (0.6)[4] | 6/6/6 |
| JG | 5.3 (0.7)[4] | 6/6/6 |
| Hyperimmune steers | | |
| 926 | 3.0 (0.6)[5] | 0/3/4 |
| 921 | 3.4 (0.4)[5] | 0/6/6 |
| Human | | |
| 1 | 6.5 (0.7)[4] | 6/6/6 |
| 2 | 5.0 (0.4)[4] | 6/6/6 |

[1]Serum samples from various sources described in Table I.
[2]Cyst sizes were determined from geometric mean diameters.
[3]Number of cysts morphologically transformed/number of surviving cysts/number of grafts attempted.
[4]Mean cyst size significantly different (p5 < 0.05) from BPV-1 -infected treatment group of (positive control for neutralization).
[5]Mean cyst size significantly different (p < 0.05) from rabbit anti-intact BPV-1 (previously used as positive control for BPV-1 xenograft neutralization studies).
[6]Mean cyst size significantly different (p < 0.05) from normal rabbit serum (previously used as negative control for BPV-1 xenograft neutralization studies).

TABLE III

NEUTRALIZATION OF BPV-1 INFECTION OF C127 CELLS BY BOVINE, RABBIT AND HUMAN SERA AND MURINE MAbs

| Serum or MAb samples[1] | Neutralization titer[2] |
|---|---|
| Vaccinated calves | |
| 163 | |
| Pre-bleed | 0 |
| 1 | 0 |
| 2 | $<10^1$ |

TABLE III-continued

NEUTRALIZATION OF BPV-1 INFECTION OF C127 CELLS BY BOVINE, RABBIT AND HUMAN SERA AND MURINE MAbs

| Serum or MAb samples[1] | Neutralization titer[2] |
|---|---|
| 173 | |
| Pre-bleed | 0 |
| 1 | 0 |
| 2 | $<10^1$ |
| Rabbit | |
| NRS | 0 |
| BPV-1 | $10^6$ |
| BPV-2 | $10^2$ |
| BPV-1 (SDS) | 0 |
| MAbs | |
| 13D6 | 0 |
| JG | 0 |
| Hyperimmune steers | |
| 926 | $>10^6$ |
| 921 | $>10^3$ |
| Human | |
| 1 | 0 |
| 2 | 0 |

[1]Identification of different sera and MAbs as in Table I.
[2]The neutralization titer is expressed as the reciprocal of the highest serum dilution required to neutralize focus formation of murine C127 cells by BPV-1 virions.

Discussion

The xenograft system has provided an effective model for the detection of antibody-mediated neutralization of productive PV infections, including BPV-1 (Christensen, N. and Kreider, J. W., *Antibody-mediated neutralization in vitro of infectious papillomaviruses. J. Virol.* 64:3151-3156 (1990)). However neutralizing antibodies also prevent BPV-1 virions from inducing FF in non-productively infected murine C127 cells in culture (Dvoretzky, I., Shober, R., Chattopadhy, S. K. and Lowy, D. R., *A quantitative in vitro focus-forming assay for bovine papillomavirus. Virology* 103:369-375 (1980)). To compare the specificity of the 2 methods, and to determine the epitopes responsible for neutralization, selected sera from cattle, rabbits and humans and murine MAbs were tested for neutralizing activity.

The papillomavirus genomes are encapsidated by L1 (major capsid) and L2 (minor capsid) proteins (Banks, L. Matlashewski, G. Pim, D., Churcher, M., Roberts, C. and Crawford, L., *Expression of human papillomavirus type-6 and type-15 capsid proteins in bacteria and their antigenic characterization. J. Gen. Virol.* 69:3081-3089 (1987), Christensen, N. Kreider, J. W., Cladel, N. M. and Galloway, D. A., *Immunological cross-reactivity to laboratory-produced HPV-11 virions of polysera raised against bacterially derived fusion proteins and synthetic peptides of HPV-6b and HPV-16 capsid proteins. Virology* 175:1-9 (1990), Cowsert, L. M., Lake, P. and Jenson, A. B., *Topographical and conformational epitopes of bovine papillomavirus type* 1 *defined by monoclonal antibodies. J. Nat. Cancer Inst.* 79:1053-1057 (1987), Cowsert, L. M., Pilacinski, W. P. and Jenson, A. B., *Identification of the bovine papillomavirus L1 gene product using monoclonal antibodies. Virology* 165:613-615 (1988), Doobar, J. and Gallimore, P. H., *Identification of proteins encoded by the L1 and L2 open reading frames of human papillomavirus* 1*a. J. Virol.* 61:2793-2799 (1987), Jin. X. W., Cowsert, L., Pilacinski, W. and Jenson, A. B., *Identification of L2 open reading frame gene products of bovine papillomavirus type-*1 *by monoclonal antibodies. J. Gen. Virol.* 70:1133-

1140 (1989), Komly, C. A., Breitburd, F., Croissant, O. and Streeck, R. E., *The L2 open reading frame of human papillomavirus type 1a encodes a minor structural protein carrying type-specific antigens. J. Virol.* 60:813, 816 (1986), Kreider, J. W., Howett, M. K., Wolfe, S. A., Barlett, G. L., Zaino, R. J., Sedlacek, T. V. and Mortel, R., *Morphological transformation in vitro of human uterine cervix with papillomavirus from condylomata acuminata. Nature* (Lond.) 317:639-640 (1985), Nakai, Y., Lancaster, W. D., Lim, L. Y. and Jenson, A. B., *Monoclonal antibodies to genus-and type-specific papillomavirus structural antigens. Intervirology* 25:30-37 (1986), Roseto, A., Pothier, P., Guillemin, M. C., Peries, J., Breitburd, F., Bonneaud, N. and Orth, G., *Monoclonal antibody to the major capsid protein of human papillomavirus type 1. J. Gen. Virol.* 65:1319-1324 (1984)), to form virions in the nuclei of terminally differentiating keratinocytes (Firzlaff, J. M., Kiviat, N. B., Beckmann, A. M., Jenison, A. and Galloway, D. A., *Detection of human papillomavirus capsid antigens in various squamous epithelial lesions using antibodies directed against the L1 and L2 open reading frames. Virology* 164:467-477 (1988), Jenson, A. B., Rosenthal, J. D., Olson, C., Pass, F. W., Lancaster, W. D. and Shah, K., *Immunologic relatedness of papillomaviruses from different species. J. Nat. Cancer Inst.* 64:495-500 (1980), Lim, P. S., Jenson, A. B., Cowsert, L., Nakai, Y., Lim, L. Y. and Sundberg, J., *Distribution and specific identification of papillomavirus major capsid protein epitopes b immunocytochemistry epitope scanning of synthetic peptides. J. Infect. Dis.* 162: 1263-1269 (1990), Sandberg, J. P., Junge, R. E. and Lancaster, W. D., *Immunoperoxidase localization of papillomaviruses in hyperplastic and neoplastic epithelial lesions of animals. Amer. J. Vet. Res.* 45:1441-1446 (1984)). The PV L1 capsid protein in contrast to the L2 protein, is highly conserved throughout the PV genus (Baker, C. C., *Sequence analysis of papillomavirus genomes, In*: N. P. Salzman and P. M. Howley (eds.), The papoviridae, Vol. 2, The papillomaviruses, pp. 321-385, Plenum, N.Y. (1987). However only type-specific and minimally cross-reactive linear and conformational epitopes of the L1 protein have been detected on the virion surface by MAbs, Cowsert, L. M., Lake, P. and Jenson, A. B., *Topographical and conformational epitopes of bovine papillomavirus type 1 defined by monoclonal antibodies. J. Nat. Cancer Inst.* 79:1053-1057 (1987), Cowsert, L. M., Pilacinski, W. P. and Jenson, A. B., *Identification of the bovine papillomavirus L1 gene product using monoclonal antibodies. Virology* 165:613-615 (1988) whereas type-specific linear epitopes of the L2 protein appear to be internal to the capsid (Jin. X. W., Cowsert, L., Pilacinski, W. and Jenson, A. B., *Identification of L2 open reading frame gene products of bovine papillomavirus type-1 by monoclonal antibodies. J. Gen. Virol.* 70:1133-1140 (1989), Komly, C. A., Breitburd, F., Croissant, O. and Streeck, R. E., *The L2 open reading frame of human papillomavirus type 1a encodes a minor structural protein carrying type-specific antigens. J. Virol.* 60:813, 816 (1986), Tomita, Y., Shirasawa, H., Sekine, H. and Simizu, B., *Expression of human papillomavirus type 6b L2 open reading frame in Escherichia coli::L2-β-galactosidase fusion proteins and their antigenic properties. Virology* 158:8-14 (1987)). In this study, only sera from rabbits immunized with either intact BPV-1 or BPV-2 virions and cattle infected with homogenates of productively infected fibropapillomas were capable of neutralizing infectivity of BPV-1 in both murine C127 cells and in the xenografts.

Although the neutralization assay in murine C127 cells may be more quantitative, primarily because the assay involves FF of single cells in a monolayer, it is no more specific than the xenograft system (Christensen, N. and Kreider, J. W., *Antibody-mediated neutralization in vitro of infectious papillomaviruses. J. Virol.* 64:3151-3156 (1990)), which is more analogous to neutralization of BPV-1 infection in the natural host by prior vaccination with intact virions (Jarrett, W. F. H., O'Neill, B. W., Gaukroger, J. M., Laird, H. M., Smith, K. T. and Campo, M. S., *studies on vaccination against papillomaviruses: a comparison of purified virus, tumour extract and transformed cells in prophylactic vaccination. Vet. Rec.* 126:449-452 (1990a), Jarrett, W. F. H., O'Neill, B. W., Gaukroger, J. M., Laird, H. M., Smith, K. T. and Campo, M. S., *Studies on vaccination against papillomaviruses: the immunity after infection and vaccination with bovine papillomaviruses of different types. Vet. Rec.* 126:473-475 (1990b)). Bovine sera from vaccinated calves almost 2 months after challenge with BPV-1 virions neutralized BPV-1-induced FF of C127 cells, but did not prevent the development of fibropapillomas in the xenografts. Although both assays were accomplished using aliquots of the same sera, the differences in personnel, handling of specimens, conditions of infection and neutralization, which were performed at separate locations, could also explain the slight difference in results.

Rabbit and bovine sera that were prepared against either denatured BPV-1 capsids or recombinant BPV-1 L1 vaccine, respectively, did not neutralize BPV-1 infectivity in either neutralization assay. Since these sera only recognized continuous BPV-1 L1 epitopes, it was concluded that linearized BPV-1 surface epitopes were not capable of inducing neutralizing antibodies. Neutralizing activity in this study appears to be largely dependent upon conformational epitopes.

The 2-human sera that reacted with intact BPV-1 particles did not prevent BPV-1-induced FF in C127 cells or transformation of bovine fetal skin in the xenograft model. This suggests that human sera either recognized a non-neutralizing mimeotope or defined BPV-1 conformational epitopes that are not associated with neutralization of BPV-1 infectivity. Nevertheless, these results support the concept that significant exposure to intact BPV-1 viral particles is necessary for the production of neutralizing antibodies (Jarrett, W. F. H., O'Neill, B. W., Gaukroger, J. M., Laird, H. M., Smith, K. T. and Campo, M. S., *studies on vaccination against papillomaviruses: a comparison of purified virus, tumour extract and transformed cells in prophylactic vaccination. Vet. Rec.* 126: 449-452 (1990a), Jarrett, W. F. H., O'Neill, B. W., Gaukroger, J. M., Laird, H. M., Smith, K. T. and Campo, M. S., *Studies on vaccination against papillomaviruses: the immunity after infection and vaccination with bovine papillomaviruses of different types. Vet. Rec.* 126:473-475 (1990b)).

Our study reveals that neutralization of BPV-1 infectivity by serum antibodies can be measured by prevention of either FF in C127 cells or transformation of bovine fetal skin in the xenograft model. Since the results of the 2 assays were concordant, it is concluded that (1) neutralization of FF of C127 cells and transformation of bovine fetal skin in the xenografts both appear to be true indicators of the capacity of antibodies to neutralize BPV-1 infectivity, that is, the antibodies react with conformationally correct L1 protein; and (2) neutralization of FF by C127 cells can be used for studies of early BPV-1 virion-host cell interaction to define functional epitopes.

Example 2

Expression of a Prototype L1 Protein (HPV-1) by the pSVL Vector Transfected into Cos Cells The L1 protein of HPV-1 was expressed because there exist several monoclonal antibodies against HPV-1 which react with conformational epitopes present on the intact virion. We reasoned that if we were successful in generating HPV-1 L1 protein with native conformation, these monoclonal antibodies might react with the isolated, expressed L1 protein. This would confirm the ability to produce L1 protein of suitable conformation to mimic that present on the intact virus particle. It is critical to generate an immune response against the conformational epitopes of the papillomaviruses in order to produce a neutralizing antibody.

The choice of vector was based upon several criteria. We desired to have expression vectors which produced high levels of capsid protein which would not only facilitate their use for vaccines but also potentially aid in achieving empty capsid formation in the nucleus. The pSVL vector and the baculovirus vectors both use very strong promoters and have been used extensively for expressing proteins. In addition, the pSVL vector contains an SV40 origin of replication and, when transfected in cos cells which express Large T antigen, replicates to high copy number. The replication of the input vector, combined with the strong activity of the viral promoter, results in extremely high levels of expressed protein. The cos cells are also permissive for the assembly of SV40 virions and might potentially facilitate the assembly of PV particles. The baculovirus system also offers the advantage that a larger percentage of cells can be induced to express protein (due to the use of infection rather than transfection techniques). While baculovirus is an insect virus and grows in insect cells (Sf9), these cells retain many of the eucaryotic mechanisms for processing of proteins (glycosylation and phosphorylation) which might be important for generating proteins of appropriate conformation.

Figure 1:
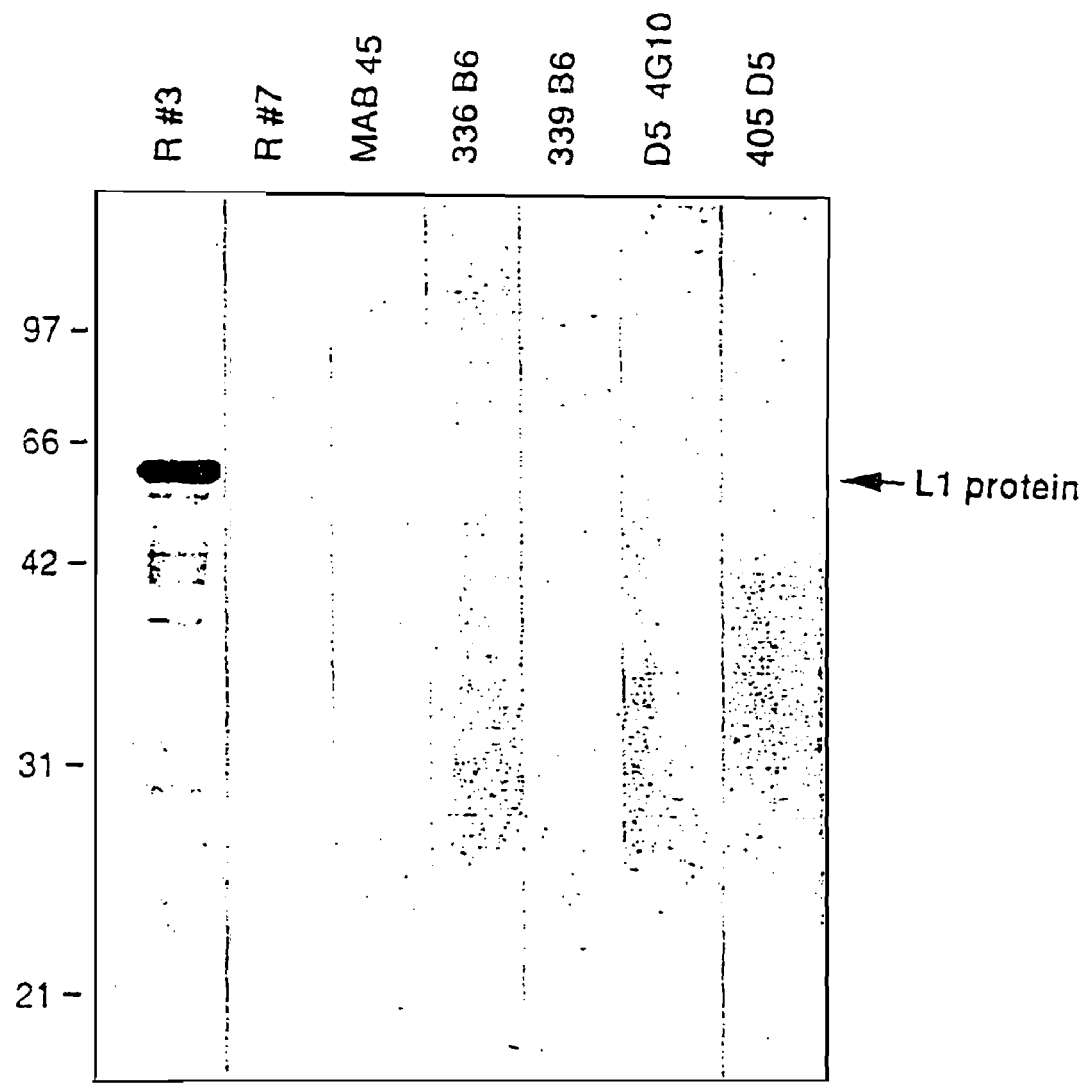
FIG. 1. Reactivity of rabbit polyclonal antisera and mouse monoclonal antibodies with SDS-disrupted HPV-1 as determined by immunoblot analysis.

The scheme for the cloning of the HPV-1 L1 protein into pSVL is shown in FIG. 1.

The expression of the HPV-1 L1 protein by pSVL was first assayed by immunofluorescence. Cos cells were transfected with 1-10 ug of the plasmid shown in FIG. 1. After 48 hrs, the cells were fixed with cold methanol and then reacted with either non-immune mouse ascites (a), rabbit antiserum generated against SDS-disrupted BPV-1 (b), or mouse monoclonal antibody 405D5 which recognizes a type-specific, conformational epitope on HPV-1. A positive nuclear staining was seen with both antibodies and was absent from non-transfected cells. In addition, the L1-expressing cells were also reactive with several additional monoclonal antibodies which specifically react with independent, conformational epitopes (data not shown). After transfection cos cells were then fixed with methanol and stained for reactivity with either control rabbit serum, Dako antiserum generated against SDS-disrupted BPV-1 virions, or mouse monoclonal antibody 405D5 which reacts specifically with HPV-1 virion conformational epitopes. Four additional conformation-specific monoclonal antibodies gave an identical immunofluorescence pattern and clearly indicate that the L1 protein synthesized in cos cells retains conformational epitopes. In addition, the L1 protein exhibits the anticipated intranuclear localization, reflecting the appropriate processing and translocation of this protein. This result demonstrates that the conformational epitope identified by 405D antibody is present entirely on the L1 protein (rather than L2 or a combination of L1/L2). Most importantly, the reactivity of L1 with this monoclonal antibody demonstrates the L1 protein has retained a conformational epitope identical to that found in its virion-associated state. Electron microscopy experiments are currently being performed to evaluate whether the L1 protein is assembling into empty viral particles. Thus, the pSVL vector is successful in producing HPV-1 L1 protein with a native conformation for generating antibody responses which react with intact virus particles.

The synthesis of the L1 protein was also determined by immunoprecipitation from transfected cos cells. At 48 hr post-transfection, the cos cells were metabolically labelled with S-35 methionine and cysteine for 4 hrs, extracted with RIPA buffer, and immunoprecipitated with rabbit antiserum generated against SDS-disrupted BPV-1 (Dako). We used this antibody for immunoprecipitations since the solubilization of L1 protein with denaturing detergents may abolish its recognition by the conformation-dependent L1 antibody described above. An SDS-PAGE of the immunoprecipitates indicates that the synthesized L1 protein is full-length (55 kD). This series of immunofluorescence and immunoprecipitation experiments demonstrates therefore that the pSVL vector will be able to generate L1 protein which will be suitable for inducing conformation-dependent antibodies.

Example 3

Papillomavirus infections cause cutaneous warts and mucosal condylomata in a wide variety of vertebrate animals (Olson, C., in "The papovaviridae" (N. P. Salzman and P. M. Howley, Eds.), pp. 39-66, Plenum Press (1987)) and, in humans, are strongly associated with the development of cervical dysplasia and carcinoma (Jenson, A. B., and Lancaster, W. D., in "Papillomaviruses and human cancer" (H. Pfister, Ed.) pp. 11-43, CRC Press (1990)). Each papillomavirus type is highly species-specific and preferentially infects squamous epithelium at a restricted number of anatomic locations. Vegetative viral DNA replication occurs in the nucleus of terminally differentiated keratinocytes where the viral genome becomes encapsidated by the major (L1) and minor (L2) capsid proteins, forming virions 55 nm in diameter. Unfortunately, there are no tissue culture systems which permit sufficient keratinocyte differentiation to propagate papillomaviruses in vitro and this limitation has compromised the analysis of the late expression of the L1 and L2 genes as well as the characterization of the host immune response to their gene products.

Due to the etiologic role that human papillomaviruses (HPV's) play in some human malignancies, recent attention has been focused on the development of a recombinant capsid protein vaccine to reduce the incidence of HPV infection and its neoplastic sequelae. The first animal model for a potential vaccine utilized bovine papillomavirus type 1 (BPV-1). The L1 protein of BPV-1 was expressed in bacteria (Pilacinski, W. P., Glassmam, D. L., Krzyzek, R. A., Sadowski, P. L., and Robbins, A. K., Biotechnology 2:356-360 (1984)) and used to immunize cattle against subsequent viral challenge (Pilacinski, W. P., Glassmam, D. L., Glassman, K. L., Read, D. E., Lum, M. A., Marshall, R. F., and Muscoplat, C. C., In "Papillomaviruses: molecular and clinical aspects" (T. R. Broker and P. M. Howley, Eds., pp. 257-271, Alan R. Liss, Inc., New York (1985)). However, since the expressed L1 protein apparently lacked native conformation (due to the insoluble, aggregate form of over-expressed, fusion proteins in bacteria), it did not induce antibodies which could either recognize or neutralize intact BPV-1 virions (Jin, X. W., Cowsert, L., Marshall, D., Reed, D., Pilacinski, W., Lim, L. Y., and Jenson, A. B., Intervirology 31:345-354 (1990); and Ghim, S., Christensen, N. D., Kreider, J. W., and Jenson, A. B., Int. J. Cancer 49:285-289 (1991)).

The ability of antibodies to neutralize papillomaviruses appears to be related to their ability to react with type-specific, conformational epitopes on the virion surface (Ghim, S., Christensen, N. D., Kreider, J. W., and Jenson, A. B., Int. J. Cancer 49:285-289 (1991); Christensen, N. D. and Kreider, J. W., J. Virol. 64:3151-3165 (1990); Christensen, N. D., Kreider, J. W., Cladel, N. M., Patrick, S. D., and Welsh, P. A., J. Virol. 64:5678-5681 (1990); and Jarrett, W. F. H., O'neil, B. W., Gaukroger, J. M., Smith, K. T., Laird, H. M., and Campo, M. S., Vet. Rec. 126:437-475 (1990)) and, indeed, previous studies have demonstrated that the predominant antibody response detected against HPV-1 in humans is directed against such conformational epitopes (Steele, J. C., and Gallimore, P. H., Virology 174:388-398 (1990); and Anisimová, E., Barták, P., Vlcek, D., Hirsch, I., Brichácek, B., and Vonka, V., J. Gen. Virol. 71:419-422 (1990)). In the current study, we characterize a series of antibodies for their reactivity with HPV-1 conformational epitopes and demonstrate that HPV-1 µl protein synthesized in cos cells expresses these virion conformational epitopes. This expressed protein can, therefore, be used for vaccine development as well as serologic screening techniques.

The initial experiments were designed to characterize a series of polyclonal and monoclonal antibodies for their reactivity with HPV-1 virions which were either in an intact (native conformation) or SDS-denatured (non-conformational) state. It was essential to characterize these antibodies in detail so that they could be used to evaluate the conformational state of expressed HPV-1 L1 protein. A summary of the ELISA experiments and the details for the isolation and purification of the HPV-1 virions are given in Table IV. Briefly, microtiter plate wells were coated with either intact or SDS-disrupted HPV-1 virions as described previously (Cowsert, L. M., Lake, P., and Jenson, A. B., J. Natl. Cancer Inst. 79:1053-1057 (1987)) and used to screen the indicated antisera or monoclonal antibodies. The two hyperimmune rabbit sera produced against HPV-1 have been described previously (Pass, F., and Maizel, J. V., J. Invest. Dermatol. 60:307-311 (1973)); rabbit (R #3) antiserum was generated against disrupted HPV-1 particles and rabbit (R #7) antiserum against intact particles. The four monoclonal antibodies that recognize conformational epitopes on the surface of HPV-1 particles were kindly provided by Dr. P.

TABLE IV

Reactivity of rabbit polyclonal antisera and murine monoclonal antibodies with intact and disrupted HPV1 virions[a] as determined by ELISA.

| Antibody | Immunogen | | ELISA value | |
|---|---|---|---|---|
| | | Intact virions | Disputed virions | |
| Rabbit | Pass #7 | intact HPV1 | 1.493 | 0.002 |
| | Pass #3 | disrupted HPV1 | 0.918 | 0.616 |
| Murine | 334B6 | intact HPV1 | 0.438 | 0.003 |
| | 339B6 | intact HPV1 | 0.520 | 0.000 |
| | 405D5 | intact HPV1 | 0.429 | 0.009 |
| | D5 4G10 | intact HPV1 | 0.464 | 0.003 |
| | MAB45[b] | L1 of HPV1 | 0.512 | 0.332 |

[a]HPV-1 virions were extracted from productively infected plantar warts (Jenson, A.B., Lim, L.Y., and Singer, E., J. Cutan. Pathol. 16:54-59 (1989)) and purified by equilibrium centrifugation in a CsCl gradient (Cowsert, L.M., Lake, P., and Jenson, A.B., J. Natl. Cancer Inst. 79:1053-1057 (1987)). Virions (1.34 g/ml) and empty particles (1.29 g/ml) were collected separately, dialysed against Tris buffer (20 mM Tris, 10 mM PMSF, pH 7.5) and stored at −70° C.. Microtiter plate wells (Immunolon II, Dynatech) were coated with either #intact or SDS-disrupted HPV-1 virions as described previously (Cowsert, L.M., Lake, P., and Jenson, A.B., J. Natl. Cancer Inst. 79:1053-1057 (1987)). The plates were then washed with PBS containing 0.05 % Tween 20 (PBST). The microtiter wells were further incubated with PBS containing 1% bovine serum albumin (PBSA) for 1 hr at 37° C. to prevent nonspecific protein binding. The plates were washed again with PBST and incubated first with either rabbit polyclonal antibodies or murine monoclonal antibodies as primary #antibody and subsequently with appropriate alkaline phosphatase-conjugated goat andi-IgG diluted 1:1000 in PBSA (Bio-Rad) for 1 hr at 37° C.. Following several washes, the microtiter plates were developed with SIGMA 104 phosphatase substrate (Sigma) in diethanolamine buffer (Voller, A., Bidwell, D., and Bartlett, A., In "Manual of clinical immunology" (N. Rose and H. Freedman, Eds.), pp. 359-371. American Society of Microbiology, Washington, DC (1980)) for 30 min at 37° C.. Absorbance was measured at 410 nm using #a Dynatech Micro-elisa reader.
[b]MAB45 is an abbreviated designation for MABDW45 (Yaegashi, N., Jenison, S.A., Valentine, J.M., Dunn, M., Taichman, L.B., Baker, D.A., and Galloway, D.A., J. Virol. 65:1578-1583 (1991)).

(MAB45) defines a linear epitope on the surface of the HPV-1 virion (Yaegashi, N., Jenison, S. A., Valentine, J. M., Dunn, M., Taichman, L. B., Baker, D. A., and Galloway, D. A., J. Virol. 65:1578-1583 (1991)) and was obtained through the generosity of Dr. D. A. Baker (State University of New York, Stony Brook). The ELISA data indicate that R#7 antiserum indeed is specific for conformational epitopes on the surface of the HPV-1 virion since it reacts only with intact HPV-1 virions. This is also true for monoclonal antibodies 334B6, 339B6, 405D5, and D54G10. On the other hand, R#3 antiserum and monoclonal MAB45 also react well with SDS-denatured virions, demonstrating their reactivity with linear, non-conformational epitopes (Cowsert, L. M., Lake, P., and Jenson, A. B., J. Natl. Cancer Inst. 79:1053-1057 (1987)).

To confirm the ELISA results shown in Table IV, we also evaluated the same antibodies for reactivity with disrupted HPV-1 virions as determined by Western blotting (FIG. 1). This figure demonstrates that only antibodies which recognized denatured HPV-1 virions by ELISA (R#3 and MAB45) showed significant reactivity with SDS-denatured virion proteins by immunoblotting. However, antibodies shown in Table IV to recognize only intact virions (R#7, 334B6, 339B6, D54G10, and 405D5) exhibited no or little reactivity by immunoblotting analysis. Thus, two independent techniques verify the specificity of the above antibodies for conformational and non-conformational epitopes on the HPV-1 virion.

In an attempt to produce isolated L1 protein which retained critical virion conformation epitopes, we expressed the HPV-1 L1 protein in mammalian cells. The HPV-L1 gene was amplified by PCR and cloned into the pSVL vector as described in FIG. 2 using standard molecular techniques (Maniatis, T., Fritsch, E. F., and Sambrook, J., In "Molecular cloning: A laboratory manual" Cold Spring Harbor Laboratory, Cold Spring Harbor, N.Y. (1989)). The resulting plasmid, pSJ1-L1, expresses the HPV-1 L1 gene from a strong SV40 late promoter. In addition, the plasmid also contains the SV40 origin of replication and, when transfected into cos cells by calcium phosphate precipitation (Graham, F. L., and van der Eb, A. J., Virology 52:456-467 (1973)), replicates to a high copy number.

Cos cells were first evaluated for L1 protein synthesis by immunoprecipitation techniques using the above antibodies. 48 hr post-transfection, the cos cells were labelled with $^{35}$S-methionine (NEN, Express $^{35}$S Protein labelling Mix) for 4 hr, washed with buffer, and solubilized in RIPA buffer (which contains a mixture of 1% NP-40, DOC, and 0.1% SDS detergents). The cell extracts were then immunoprecipitated with the indicated antibodies and analyzed by SDS-gel electrophoresis as previously described (Goldstein, D. J., and Schlegel, R., EMBO 9:137-146 (1990)). The data in FIG. 3 indicate that L1 protein could be efficiently precipitated by conformation-dependent antibodies (such as R#7, 334B6, 339B6, D54G10 and 405D5). In addition, the L1 protein could also be immunoprecipitated with antibodies which recognize non-conformational epitopes on the virion surface (R#3). These findings indicate that the L1 protein expressed in cos cells displayed conformational epitopes observed previously only on intact virions. It is also obvious that the L1 extraction conditions did not significantly denature the protein. Characteristic of L1 protein isolated directly from virions, the synthesized L1 protein was approximately 57 kD in size (Doorbar, J., and Gallimore, P. H. J. Virol. 61:2793-2799 (1987)). The retention of conformational epitopes in RIPA buffer and the ability of conformation-dependent antibodies to react with L1 indicates that the affinity purification of L1 protein from transfected cells will be possible.

Cos cells were also evaluated for L1 protein synthesis by immunofluorescence microscopy (FIG. 4). Cells, plated onto glass coverslips in Dulbecco's modified Eagles medium (DMEM) supplemented with 10% fetal calf serum, were transfected with 10 µg plasmid DNA, glycerol-shocked 48 hr later, washed with phosphate buffered saline (PBS), and fixed for 5 min in cold acetone. The cells were then reacted with appropriate dilutions of primary antibody followed by fluorescein-conjugated goat anti-rabbit or goat anti-mouse IgG. Incubations with primary and secondary antibodies were performed at room temperature for 1 hr. Subsequent to a final PBS wash, the coverslips were mounted in Elvanol and viewed with an Olympus fluorescent microscope. The presence of L1 protein in cell nuclei was clearly discernible in 5-10% of transfected cells 48 hours post-transfection, independent of whether the primary antibody reacted with conformational and/or non-conformational epitopes. All of the antibodies which were capable of immunoprecipitating L1 were also successful by immunofluorescence. As mentioned previously, antibodies produced against disrupted virions recognize both internal and external virion linear epitopes and therefore are capable of reacting with intact particles (e.g., R#3). However, such antibodies do not recognize conformational epitopes and are not neutralizing (Ghim, S., Christensen, N. D., Kreider, J. W., and Jenson, A. B., Int. J. Cancer 49:285-289 (1991)). Thus, the staining pattern obtained with rabbit antisera to native (R#7) or denatured (R#3) HPV-1 virions was indistinguishable. These results, therefore, demonstrate unequivocally that the L1 protein synthesized in the cos cells was of a conformation similar to that found in intact virions. In addition, the protein clearly translocated to the nucleus in a normal fashion (Zhou, J., Doorbar, J., Sun, X. Y., Crawford, L. V., McLean, C. S., and Franzer, I. H., Virology 185:625-632 (1991)).

The above findings suggest that the HPV-1 major capsid protein, when expressed in the absence of other viral proteins, can precisely reproduce/mimic the antigenicity of intact viral particles. While we cannot be certain that no assembled viral particles are present in the transfected cos cells, we have been unsuccessful in visualizing such structures by electron microscopic examination of either transfected cells or of immunoprecipitates containing L1 protein (data not shown). Apparently it is not essential to have viral particle formation in order to reproduce the characteristic, viral conformational epitopes.

Since the neutralization sites present on papillomavirus virions consist predominantly of conformational epitopes, it is inferred in our studies that the L1 protein synthesized in cos cells might serve successfully as a vaccine or for the serologic detection and typing of papillomavirus infections. Due to the similarities among the papillomaviruses with respect to genetic organization, virion structure, and amino acid sequence of their capsid proteins, it is also likely that our findings with HPV-1 L1 will have direct applicability to the study of other HPV's such as HPV-16 and HPV-18 which have important contributory roles to the development of cervical carcinoma.

TABLE V

ELISA VALUES AT 25 MIN IN SUBSTRATE
Four rabbits wereinoculated with homogenates of COS cells containing intranuclear, conformationally correct BPV-1 L1. Each of 4 rabbits received homogenates of $1 \times 10^6$ cells in Freund's complete adjuvant on day 0, and $1 \times 10^6$ cells in Freund's incomplete adjuvant on days 14 and 28, and were then exsanguinated on day 38. Prebleed sera from the 4 rabbits were negative for reactivity with intact and denatured BPV-1 virions by ELISA. At day 38, rabbit #1 2, 3 and 4 were tested for reactivity with intact and disrupted BPV-1 particles after 25 min. incubation with substrate as shown in Table V.

|   | 1:50 | 1:100 | 1:500 |   |
|---|---|---|---|---|
| 1. | .445 | .266 | .014 | Intact BPV-1 (I) |
|   | .042 | .028 | .001 | Disrupted BPV-1(D) |
|   | .016 | .001 | −.002 | Phosphate buffer saline (PBS) |
| 2. | .332 | .210 | .011 | (I) |
|   | .076 | .047 | .077 | (D) |
|   | .025 | .018 | .001 | (PBS) |
| 3. | .157 | .096 | .003 | (I) |
|   | .027 | .016 | −.001 | (D) |
|   | .022 | .011 | −.001 | (PBS) |

TABLE V-continued

ELISA VALUES AT 25 MIN IN SUBSTRATE
Four rabbits wereinoculated with homogenates of COS cells containing intranuclear, conformationally correct BPV-1 L1. Each of 4 rabbits received homogenates of $1 \times 10^6$ cells in Freund's complete adjuvant on day 0, and $1 \times 10^6$ cells in Freund's incomplete adjuvant on days 14 and 28, and were then exsanguinated on day 38. Prebleed sera from the 4 rabbits were negative for reactivity with intact and denatured BPV-1 virions by ELISA. At day 38, rabbit #1 2, 3 and 4 were tested for reactivity with intact and disrupted BPV-1 particles after 25 min. incubation with substrate as shown in Table V.

|   | 1:50 | 1:100 | 1:500 |   |
|---|---|---|---|---|
| 4. | .275 | .159 | .011 | (I) |
|   | .075 | .044 | .005 | (D) |
|   | .017 | .011 | .001 | (PBS) |
| * 1H8 | — | — | .022 | (I) |
|   | — | — | .880 | (D) |
|   | — | — | <.020 | (PBS) |
| **Rabbit intact BPV-1 Virions | — | — | >2.000 | (I) |
|   | — | — | .058 | (D) |
|   | — | — | <.020 | (PBS) |

* MAb 1H8 recognizes only disrupted BPV-1
**Polyclonal Ab rabbit anti-intact BPV-1 recognized only intact BPV-1

Now having fully described this invention, it will be understood by those with skill in the art that this invention may be performed within a wide and equivalent range of conditions, parameters, and the like, without affecting the spirit or scope of the invention or any embodiment thereof.

All references cited herein are incorporated by reference in their entirety as if individually incorporated by reference.

What is claimed is:

1. A method of immunodetecting human papillomavirus antibodies which specifically bind native human papillomavirus L1 protein, comprising:
   providing an isolated recombinantly produced human papillomavirus (HPV) L1 protein, in the absence of human papillomavirus L2 protein, which protein exhibits the same conformational structure as the corresponding native human papillomavirus L1 protein; contacting a sample with said isolated recombinantly produced human papillomavirus L1 protein; and detecting whether said isolated recombinantly produced human papillomavirus-L1 protein specifically binds to antibodies contained in said sample.

2. The method of claim 1, wherein the sample is serum obtained from a human suspected to have a human papillomavirus infection.

3. The method of claim 1, wherein the human papillomavirus is selected from the group consisting of HPV1, HPV2, HPV3a, HPV4, HPV5, HPV6b, HPV7, HPV8, HPV9, HPV10, HPV11a, HPV12, HPV13, and HPV18.

4. The method of claim 1, wherein the isolated recombinantly produced human papillomavirus L1 protein is directly or indirectly attached to a label that provides for detection of specific binding of antibodies to the isolated recombinantly produced human papillomavirus L1 protein.

5. A diagnostic kit for detecting the presence of antibodies directed against native human papillomavirus L1 protein which comprises:
   (i) a diagnostically effective amount of an isolated recombinantly produced human papillomavirus L1 protein, in the absence of human papillomavirus L2 protein, which exhibits the same conformational structure as native human papillomavirus L1 protein expressed by a native human papillomavirus and (ii) a label that provides for detection of binding of said native human papillomavirus L1 protein, wherein said label is directly or indirectly attached to said protein.

6. The kit of claim 5, wherein the human papillomavirus is selected from the group consisting of HPV 1, HPV2, HPV3a, HPV4, HPV5, HPV6b, HPV7, HPV8, HPV9, HPV10, HPV11a, HPV12, HPV13, and HPV18.

* * * * *